United States Patent [19]

Berard et al.

[11] Patent Number: 5,170,056
[45] Date of Patent: Dec. 8, 1992

[54] OPTICAL FIBER COUPLED DEVICES FOR REMOTE SPECTROSCOPY IN THE INFRARED

[75] Inventors: Joseph R. Berard, Cranston, R.I.; Robert J. Burger, Newton Centre, Mass.; Peter J. Melling, Sturbridge, Mass.; William R. Moser, Hopkington, Mass.

[73] Assignee: Galileo Electro-Optics Corporation, Sturbridge, Mass.

[21] Appl. No.: 662,281

[22] Filed: Feb. 28, 1991

[51] Int. Cl.⁵ ............................................. G01N 21/01
[52] U.S. Cl. ............................................ 250/341
[58] Field of Search ................................... 250/341

[56] References Cited

U.S. PATENT DOCUMENTS

| | | | |
|---|---|---|---|
| 3,370,502 | 2/1968 | Wilks, Jr. ........................ | 356/133 |
| 3,393,603 | 7/1968 | Harrick .......................... | 356/246 |
| 4,595,833 | 6/1989 | Sting ............................. | 250/353 |
| 4,730,882 | 3/1988 | Messerschmidt ................ | 385/146 |
| 4,826,313 | 5/1989 | Schär et al. .................... | 356/51 |
| 4,827,121 | 5/1989 | Vidrine, Jr. et al. ............ | 356/346 |
| 4,829,186 | 5/1989 | McLachlan et al. ............. | 250/373 |
| 4,975,581 | 12/1990 | Robinson et al. ............... | 250/339 |

Primary Examiner—Constantine Hannaher
Attorney, Agent, or Firm—Watson, Cole, Grindle & Watson

[57] ABSTRACT

The invention is directed to a probe operative in the infrared region of the electromagnetic spectrum for in situ sensing of the absorption of IR energy in a sample. The probe comprises an attenuated total reflection (ATR) element having an input end and an output end for respectively receiving IR and transmitting attenuated IR. The ATR element has wall portions disposed about a central or long axis thereof for reflecting IR energy transverse to the central axis. A bundle of infrared transmitting fibers is located at the input end of the ATR element for transmitting and receiving IR energy into and out of the element. The fibers have end faces proximate the ATR element lying in a plane perpendicular to the central axis.

33 Claims, 9 Drawing Sheets

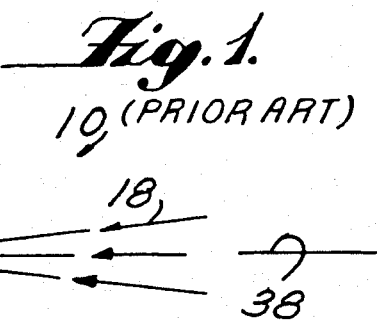
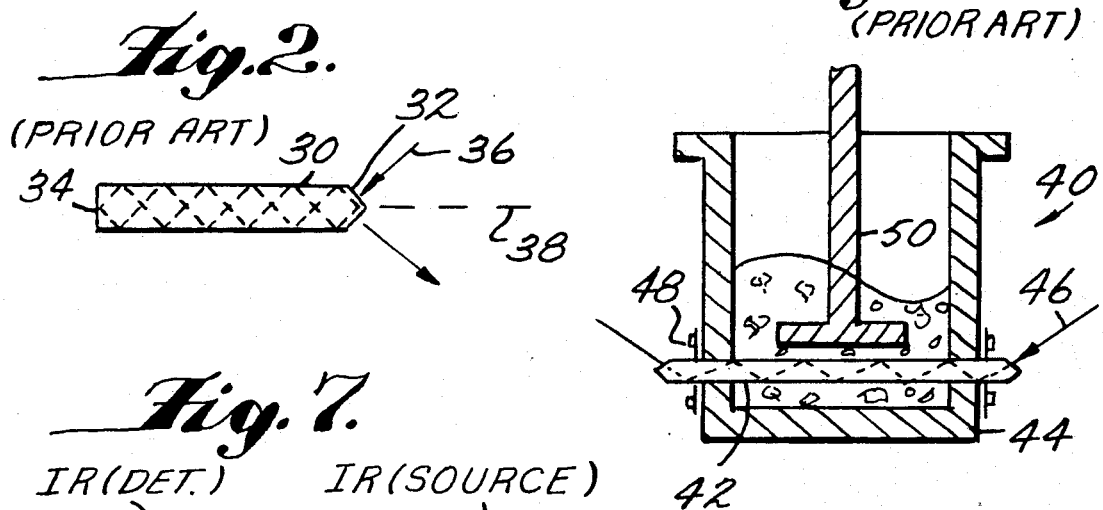
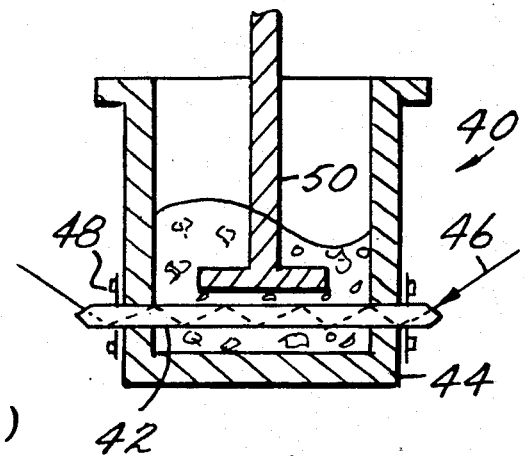
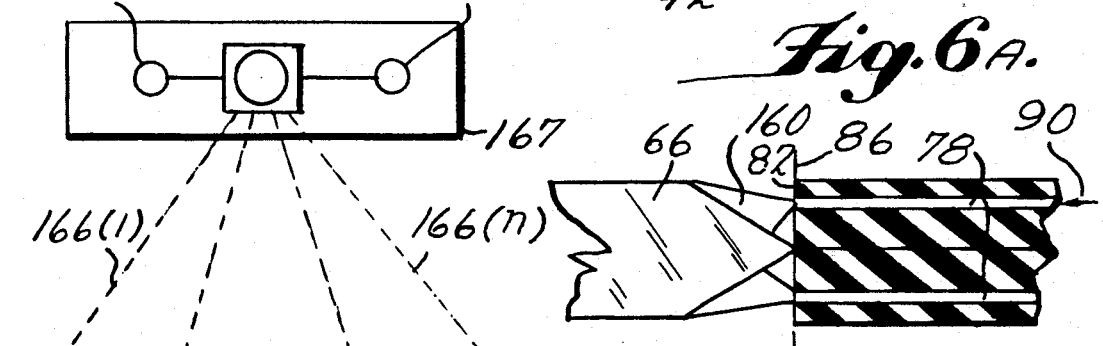
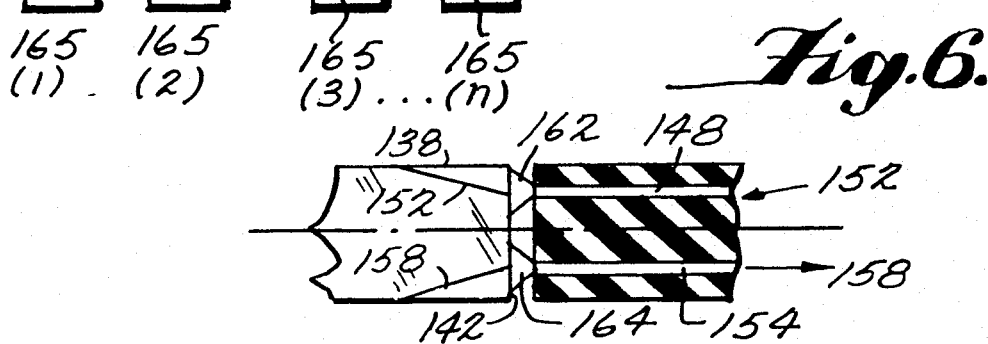

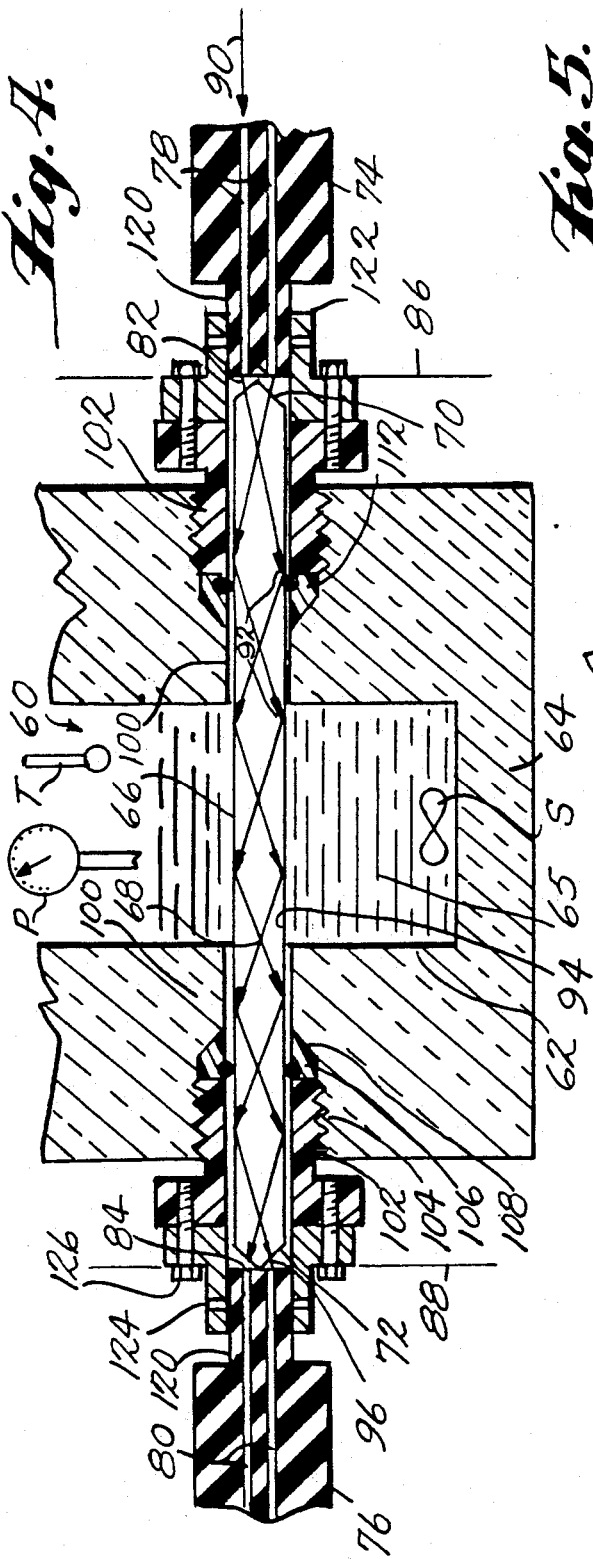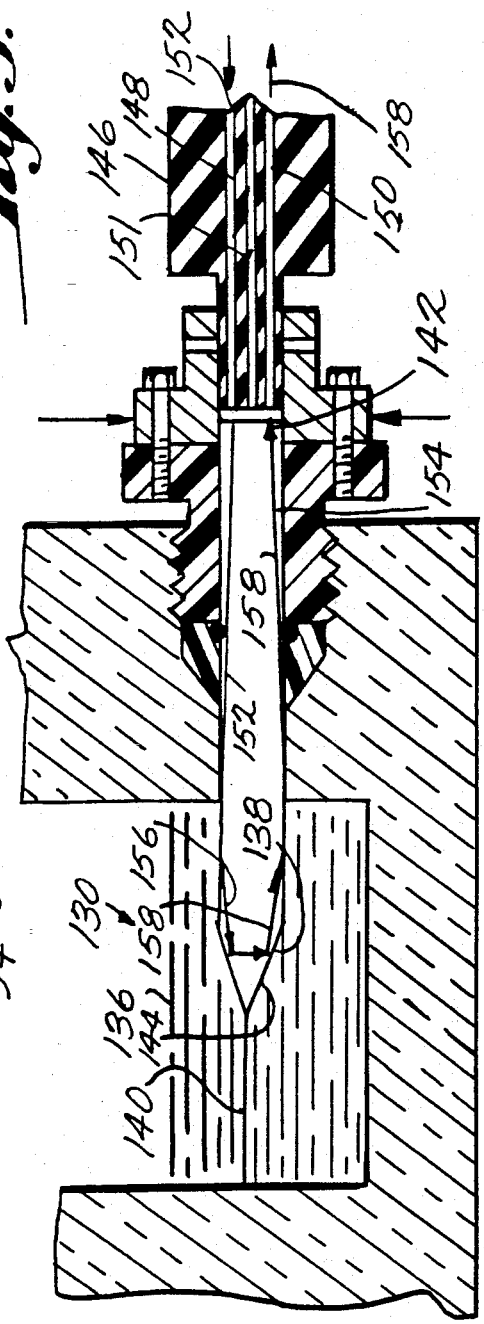

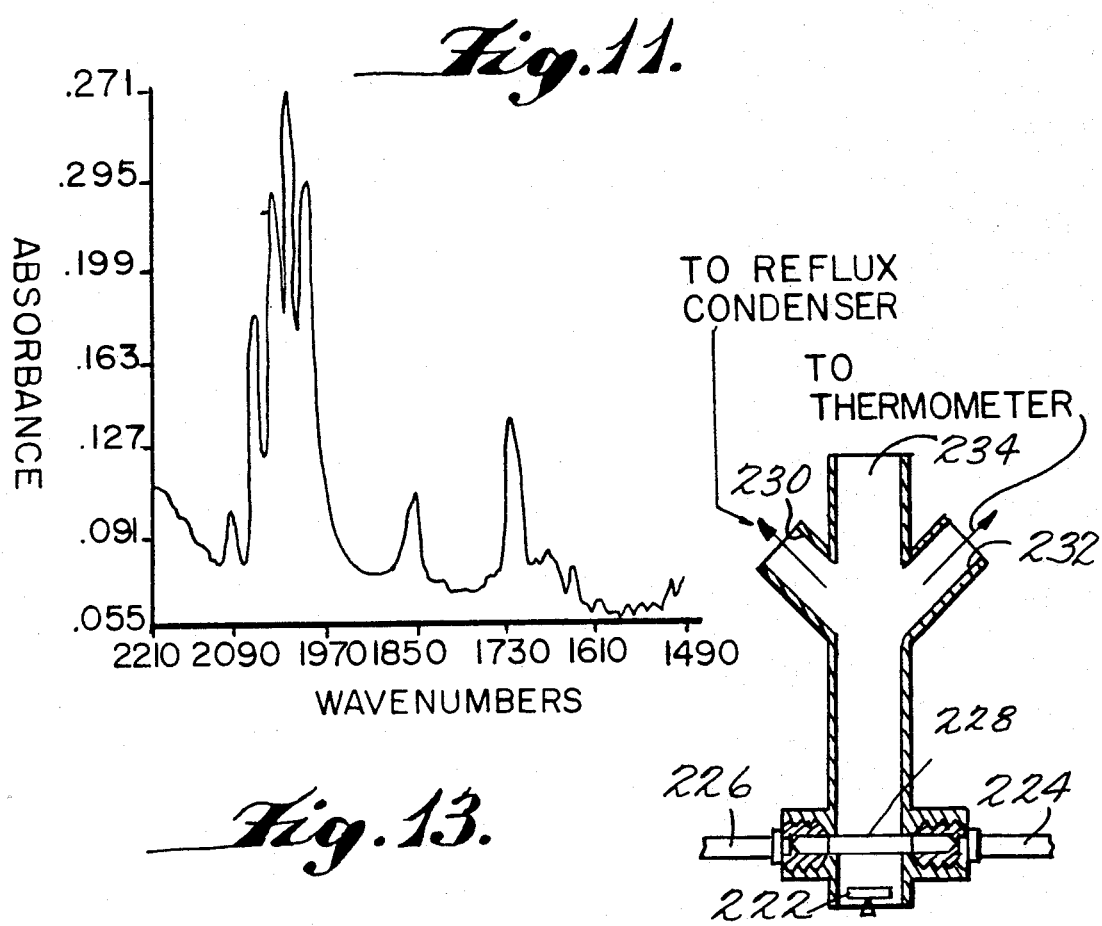
Fig.11.
Fig.12.
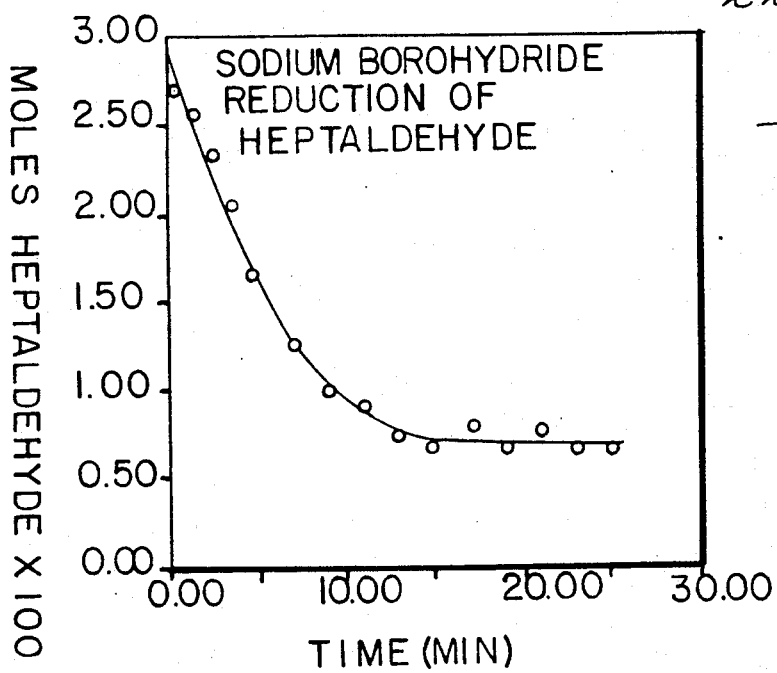
Fig.13.

ACETONE WATER BEERS LAW PLOT

OPTICAL FIBER COUPLED DEVICES FOR REMOTE SPECTROSCOPY IN THE INFRARED

FIELD OF THE INVENTION

The present invention relates to infrared spectroscopy and more particularly to the design, fabrication and application of devices incorporating flexible optical fiber bundles, for the determination of infrared spectroscopic signatures remote from the spectrometer. These devices are particularly appropriate for facilitating the determination of spectra under elevated or depressed temperatures or pressures in liquids, aqueous solutions, gels, muds, creams, pastes, oils and suspensions, and they may also be used for gases and vapors.

BACKGROUND OF THE INVENTION

In the infrared (IR) region of the electromagnetic spectrum many inorganic and almost all organic chemicals have spectra that can be used to identify them and measure their concentration in mixtures. Unlike other analytical techniques such as mass spectrometry, chromatography and wet chemistry, IR analysis is nondestructive and does not disturb the sample.

A considerable amount of quantitative and semiquantitative analysis is conducted using Fourier Transform IR (FTIR) and wavelength dispersive IR spectrometers. This work uses a variety of inconvenient and difficult to use micro cells and pumped flow cells.

The multiple internal reflection (MIR) technique has been developed and refined in order to simplify spectrographic analysis. This technique overcomes the need for very short path length transmission cells by making use of the fact that when IR radiation propagating within a transparent medium is reflected internally from a surface, a portion of the radiation extends into the surrounding medium. This distance is typically in the 1-50 μm range. As a result the intensity of the reflected light is reduced at those wavelengths at which the surrounding medium absorbs. The known art for analyzing strongly absorbing or scattering liquids uses flat plate MIR cells, very short path length transmission cells, rod crystals using refractive lenses, rod crystals using funnel shaped mirrors and cylindrical internal reflection (CIR) rods.

A known CIR device 10 shown in FIG. 1 is composed of an infrared transmitting material such as attenuated total reflection (ATR) crystal 12 which transmits light in the desired frequency range and has the geometry of a cylinder which is polished and pointed at both ends 14, 16. Usually IR radiation 18 is directed into one end 14 of the crystal 12 at a 90° angle to the pointed surface. The radiation propagates through the CIR crystal 12 and makes reflections with its polished walls 20. At each point of reflection shown by the arrows 22 an evanescent wave is formed which penetrates into the surrounding media 24 resulting in an interaction of the light wave with the medium outside of the crystal 12. After several other reflections of the light on the crystal walls 20, it passes out of the crystal at the other end 16 and is directed toward a detector 26 where the signal is analyzed. Comparison of a spectrum taken with no medium other than air to one containing inorganic or organic compounds surrounding the crystal permits the acquisition of an infrared, visible, ultraviolet or other spectrum. The CIR device 10 shown in FIG. 3 is described in Sting, U.S. Pat. No. 4,595,833 and by Wilks and Rein (P. A. Wilks Ind. Res. & Dev., 132, Sept. 1982 and by A. J. Rein and P. A. Wilks, Am. Lab. 14 (10), 153 (1982)).

Another known configuration for the crystal 30 shown in FIG. 2 is described in Harrick, U.S. Pat. No. 3,393,603. In this arrangement the crystal 30 has a pointed input/output end 32 and a flat reflector end 34 which returns the light 36.

The CIR technique may also be used for high pressure, stirred chemical reactions, as described by Moser et al. (W. R. Moser, J. E. Cnossen, A. W. Wang, and S. A. Krouse 187th National Am. Chem. Soc. Meet. April, 1984, St. Louis, MO. USA; ibid; J. Catalysis, 95, 21-23 (1985)). Known CIR-Reactors 40, such as illustrated in FIG. 3, permit limited unsatisfactory in situ reaction monitoring capabilities for a variety of catalytic reactions including heterogeneous gaseous solid reactions at high temperature and pressure. The ATR element 42 is located in high pressure vessel 44 as shown. The incident beam 46 enters the crystal 42 at one end, is attenuated and exits at the other end. The crystal is secured at the vessel 44 by means of step pressure seals 48. The stirrer 50 is provided to facilitate the reaction. It has also been proposed that CIR-Reactors may be used to provide reaction monitoring of zeolite synthesis, sol-gel inorganic oxide synthesis, and have the potential for monitoring biological systems which are usually studied in aqueous media.

The application of spectroscopy to chemistry and process control using NIR and IR spectrophotometers, FTIR, other spectrometers plus single point and multiple frequency measurement systems has been mainly restricted to the laboratory environment due to the lack of availability of convenient mechanisms for remotely locating measurement cells from instrument housings. There are several examples of locally mounted attachments for UV, visible and IR spectrometers that are commercially available and described in the literature and patents (see for example Wilks Jr., U.S. Pat. No. 3,370,502 and the Harrick and Sting Patents noted above). These devices all mount into or adjacent to the sample compartment of spectrometers using mirrors and/or transmissive optics for delivering and returning the light beam from the sample cell to the instrument detector. Although the stated purpose of some of these attachments is to provide for in situ monitoring of solid, liquid or gaseous samples including chemical reactions, these samples must generally be removed from their natural environment and conveyed to the instrument for measurement. This is often inconvenient since the measurement system is usually located in a clean laboratory environment remote from the location where the sample is produced. The validity of in vitro laboratory measurement versus actual in situ environment monitoring is subject to question. Laboratory methods are typically restricted in volume and environmental conditions. The timing between sampling a process line and measuring sample properties in the laboratory may result in sample degradation and provides no information regarding the actual process product during the time between samples. Furthermore, laboratory methods can place a valuable instrument in jeopardy of contamination and/or destruction depending upon the biological, chemical or physical nature of the sample and test environment.

The various optical systems which employ a CIR rod require complex and bulky optics for assuring that the light enters the crystal at an appropriate angle with respect to the central or long axis 38 of the crystal 12, 30. This is cumbersome, inconvenient and expensive to implement. In addition, it limits the placement of spectrographic equipment to closely proximate, line of sight arrangements with the reactor. Such restrictions make it difficult if not impossible to perform in situ measurements in a hostile environment.

The prior art involves the use of reflective and transmissive optics mounted locally to a spectrometer lacking the ability to locate the sample measurement remotely from the instrument. Alternatively, the prior art employs hollow reflective tubes for conductance of spectrometer radiation to an optical condenser and remote transmission or IRE cell. See for example W. M. Doyle & N. A. Jennings Spectroscopy 5 (1) 34–38 (1990)). The hollow rigid tube waveguide approach is inflexible and has demonstrated very poor optical efficiency and limited linear performance. It is a crude design but until the advent of the present invention, it has been the best available recourse for remote testing and immersion probe testing.

SUMMARY OF THE INVENTION

It is therefore an object of the invention to provide a convenient flexible means of coupling an attenuated total reflection (ATR) element to a spectrometer so that good spectra may be obtained in moderate times from samples including those that are inconvenient or dangerous to measure in a spectrometer. A distinguishing characteristic of the invention from the prior art is the design of a family of analytical cells for remote distributed networking to a data collection and analysis center. The remote distributed network is accomplished by uniquely coupling specially designed cell(s) using fiber optics with a broad spectral window particularly in the infrared. The nonimaging character of fiber plus the optical characteristics of the cell are physically arranged so as to optimize the system for efficiency and signal to noise, thereby allowing for the collection of chemical information not previously obtainable by any other means.

In a particular embodiment, the invention is directed to a probe operative in the infrared region of the electromagnetic spectrum for in situ sensing of IR absorption in a sample. The probe comprises an attenuated total reflection (ATR) element having an input end and an output end for respectively receiving IR and transmitting attenuated IR. The ATR element has wall portions disposed about a central or long axis thereof for reflecting IR energy therealong transverse to the central axis. A bundle of infrared transmitting fibers is located at the input end of the ATR element for transmitting and receiving IR energy into and out of the element. The fibers have end faces proximate the ATR element lying in a plane perpendicular to the central axis.

In one embodiment, the input and output are at one end of the ATR element and a reflector end is located at an opposite end thereof for returning attenuated incident input IR energy to the output. In another embodiment, the reflector end is a truncated cone having a flattened end and a mirror thereon.

The fibers may be divided into input and output fibers and intermingled at the combined input/output end.

The numerical aperture of the fiber produces a wide cone of acceptance so that coupling of the IR energy between the fibers and the ATR element is accepted without intermediate optics.

BRIEF DESCRIPTION OF THE DRAWINGS

FIG. 1 is a schematic representation of a known CIR device;

FIG. 2 is a simplified representation of a known single ended crystal;

FIG. 3 is a schematic representation of a known CIR high pressure reactor;

FIG. 4 is a fragmentary sectional drawing of double ended device according to the invention;

FIG. 5 is a fragmentary view of a single ended probe according to the present invention;

FIGS. 6A and 6B are enlargements of the optical fiber MIR element interface;

FIG. 7 is a schematic block diagram of a simultaneous multiple reactor analysis system;

FIGS. 9, 10, 13 and 15 are time plots of data taken for various examples described in the specification;

FIG. 12 is an illustration of an apparatus employing the double ended probe of the invention used in one of the examples described in the specification;

FIGS. 11, 14, 16–18 and 20–21 are spectrographs taken in the various examples described in the specification using the probe of the invention.

DESCRIPTION OF THE PREFERRED EMBODIMENT

Figure 8A:
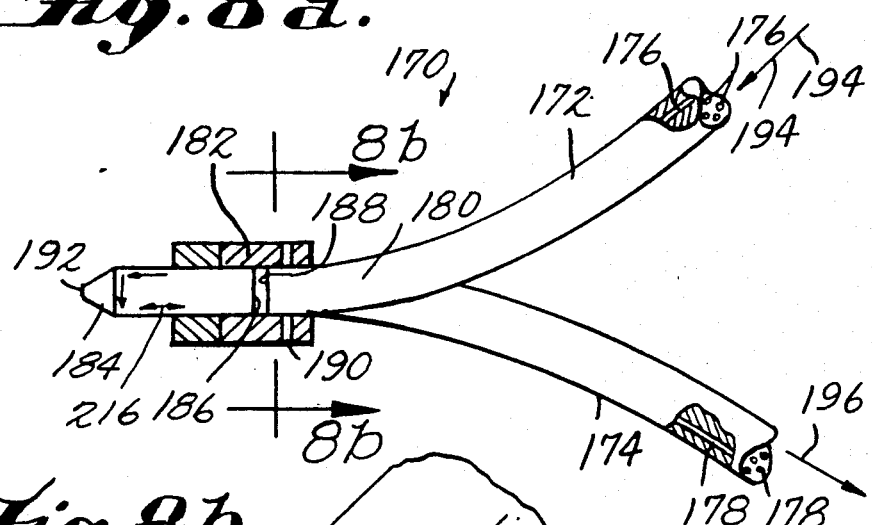
FIG. 8A is an illustration of a single ended probe having separate fiber bundles.

The invention relates to remote devices for optical spectroscopy, especially but not limited to the infrared spectrum, utilizing fiber optics coupled to attenuated total reflection (ATR), internal reflection elements (IRE) and multiple internal reflection (MIR) cells. By matching the geometrical design and orientation of the MIR cell to the numerical aperture and spatial radiative properties of a plurality of optical fibers also arranged in a special geometrical format, probe radiation can be coupled out of a spectrometer or measurement instrument, through a long fiber optic cable, into the IRE cell and then back to the instrument or directly into a remote dedicated detector system using fiber and/or bulk relay optics thereby providing a remote mechanism for probing solid, liquid or gaseous samples in situ or in a safety enclosure remote from the instrument. The fiber optic could be a single fiber but is best configured from a plurality of transmitting optical fibers in a bundle configuration of a chalcogenide glass, silver halide crystal, silica, fluoride or other IR transmitting optical fiber material. A fiber optic ferrule couples the probe to the fiber bundle.

The MIR cell is directly coupled in proximity focus contact to the fiber bundle. While a lens and reflector arrangement may be employed, the preferred embodiment is to proximity focus or butt couple the fiber optic to the MIR cell without intermediate optics in order to minimize system error. However, it is recognized that in order to eliminate problems created by thermal conduction and other environmental or process parameters it may be useful to employ a relay optic between the fiber delivery channel and the cell. The angles of the internal reflection are designed well above the critical angle for the material in order to provide for minimum distortion of the internal reflectance spectra and to accommodate a wide range of sample indices of refraction with the best overall linearity and system performance.

The interacted light radiation is then either coupled back out of the MIR cell to a return fiber optic to the detector system of the spectrometer or efficiently coupled to a local dedicated detector system at the internal reflectance cell. The signal return channel, like the delivery channel, is preferably by proximity focus to a fiber optic of similar format to the delivery channel or by use of an optical relay system either directly to the detector or to a signal channel fiber optic.

The IRE may itself function as cell for direct immersion in a container of the sample to be measured or for imbedding in a chemical process system for on-line monitoring of a process in a single ended or double ended configuration. The IRE may also be of the cylindrical internal reflectance (CIR) type for imbedding in a high pressure reactor or other type of laboratory glassware or hardware in which chemistry is routinely performed. The IRE may be made of germanium, zinc selenide, zinc sulfide, silver halide, silicon, KRS-5, or other light transmissive crystalline material, light transmissive glass or polymer material with good durability to the chemical environment. The IRE may also be coated with a thin layer of transmissive material for improved chemical or mechanical durability or the selective enhancement of the measurement of an operant or reactant. An example of the latter might be a thin surface layer containing an enzyme for specificity to a biochemical or biological specie under investigation.

Some examples of designs for remote spectrometer probe devices are described below but the application of the present invention is not limited to the described devices. The coupling of optical fibers with a CIR device has not been described in the prior art in either a pure analysis, reaction monitoring, or any other configuration. The advantages of the technique, using a reactor configuration is that the fiber coupled CIR crystal permits an easy method of embedding the active element of the device within the reactor zone of any type of chemical reactor or within the analysis zone of any type of chemical apparatus commonly employed by researchers in their study of a wide variety of chemical processes. Laboratory data developed by the inventors herein indicates that the optical fiber-CIR (OFCIR) optics are superior to prior art optics. Some of the possible configurations and equipment utilizing CIR crystals may use either a CIR crystal which is mounted within the equipment and extends through two walls, FIG. 4 or optimally it utilizes a configuration where the crystal is mounted to a single optical fiber cable and is mounted into the equipment through only one port, FIG. 5. The OFCIR of the invention has the additional advantage over the other techniques in that it affords both remote sampling and multiplexing to several analytical or reactor systems simultaneously (FIG. 7).

With specific reference to the drawings, FIG. 4 shows a fragmentary schematic illustration of a double ended MIR probe 60 located in the opposite walls 62 of a closed vessel 64 which contains a medium 65 under test. The probe 60 includes a multiple internal reflection (MIR) device in the form of an attenuated total reflection (ATR) crystal 66 having cylindrical symmetry along its central or long axis 68. The crystal 66 has conical ends 70, 72 which in this discussion are designated input and output ends respectively. Optical fiber cables 74 and 76 having respective optical waveguide fibers 78 and 80 therein are optically coupled to the corresponding ends 70 and 72, preferably in proximate butt coupled relationship as shown. The ends 82 and 84 of the fibers 78 and 80 each lie in respective planes 86 and 88 which are perpendicular to the crystal long axis 68.

In the arrangement shown, input light 90 from the fiber 78 is coupled to the crystal 66 and experiences multiple reflections at various points 92 along the walls 94 of the crystal. A portion of the input light 90 at selected wavelengths is absorbed by the medium 65. Resulting attenuated light 96 is coupled to the fibers 80 at the output end 72 of the crystal 66 for remote analysis by a spectrometer (not shown).

In a preferred embodiment, the light 90 is in the infrared (IR) or near infrared (NIR) and the fibers 78 and 80 are made of a material having a low attenuation in the region of interest.

The crystal 66 is secured in apertures 100 in the opposite walls 62 of the vessel 64 by means of threaded apertured glands 102, each of which engages a corresponding threaded bore 104 as shown. Apertured, tapered insert 106 is located in a tapered recess 108 between the bore 104 and the aperture 100. When the glands 102 are threaded into abutment with the inserts 106, the crystal 66 is sealed. Optional "O-rings" 110 may also be provided in a recess 112 formed in the insert 106.

The optical fiber cables 74 and 76 each have a stepped end portion 120 which is sized to be secured in a ferrule 122 by means of a set screw 124. The ferrule 122 is secured to the gland 102 by means of a threaded screws 126 as illustrated. Adjustment of the set screw 124 allows the respective ends 82 and 84 of the optical fiber cables 74 and 76 to be positioned with respect to the input end 70 and output end 72 of the crystal 66. The fibers 78 and 80 are preferably off the central axis 68.

FIG. 5 illustrates a probe 130 located in an apertured wall 132 of a vessel 134 which contains a medium 136 under test. The probe 130 is secured in the wall 132 in a manner essentially the same as that illustrated in FIG. 4 and will not be further described. The probe 130 includes a single ended MIR crystal 138 which has cylindrical symmetry about central or long axis 140. The crystal 138 has an input/output (I/O) end 142 and a reflector or return end 144. An optical cable 146, which includes respective input and output fibers 148 and 150, is coupled to the I/O end 142 of the crystal 138 in a manner similar to the arrangement described with respect to FIG. 4. In the arrangement of FIG. 5, however, the I/O end 142 of the crystal 138 lies in a plane essentially perpendicular to the central or long axis 140. The input and output fibers 148 and 150 are located off the central axis 140 as shown. A central fiber 151 located on the axis 140 may be employed as an output fiber to improve collection efficiency. Input light 152 is directly coupled to the I/O end 142 of the crystal 144 and experiences multiple reflections along the walls 154 of the crystal as shown. At those points of reflection 156 in the vicinity of the medium 136 a portion of the input light 152 interacts with the medium 136 is attenuated and reflected backwards into the crystal 144. Reflected and attenuated radiation 158 reverses direction at the reflector end 144 and is returned to the output fiber 150 as illustrated. Only one exemplary light path for one pair of fibers 148–150 is illustrated. However, it should be understood that many efficient paths are available for circulating the light 152 into and along the crystal 138.

FIGS. 6A and 6B illustrate in enlarged detail the relationship between an exemplary optical fiber and a crystal. FIG. 6A, for example, illustrates the interface between input fibers 78 and the double ended crystal 66 shown in FIG. 4. The fibers 78 have a numerical aperture which is a function of the optical properties and in particular the index of refraction of the fibers 78. The numerical aperture creates a cone of acceptance 160 for the fibers 78 as illustrated. Accordingly, light emanating from the fibers 78 may occur anywhere within the region defined by the cone of acceptance 160. Likewise, light entering the cone acceptance 150 will also enter the fibers 78. FIG. 6B illustrates the interface between the crystal 138 and the fibers 148 and 150 illustrated in FIG. 5. Here also, the fibers 148 and 150 each have a respective cone of acceptance 162, 164 which is defined by the numerical aperture of the corresponding fiber. Accordingly, light entering the crystal 138 must do so anywhere within the cone of acceptance 162, and likewise, light entering the fiber 150 must do so by means of the cone of acceptance 164.

In accordance with the present invention, a complicated coupling optic is not necessary in order to efficiently couple infrared light into the various MIR elements illustrated. It is not necessary as in the prior art, for example, to provide collimated or reflected light which enters the crystal at a precise angle with respect to the central axis and the input face of the crystal.

FIG. 7 illustrates a simultaneous multiple reactor analysis system employing a plurality of reactors 165(l) ... 165(n) coupled by fiber optic bundle 166(l) ... 166(n) to a Fourier Transform infrared spectrometer 167. An IR source 168 and IR detector 169 are appropriately coupled by multiplexing techniques to the various reactors 165(l) ... 165(n) so that multiple simultaneous reactions may be monitored.

Figure 8B:
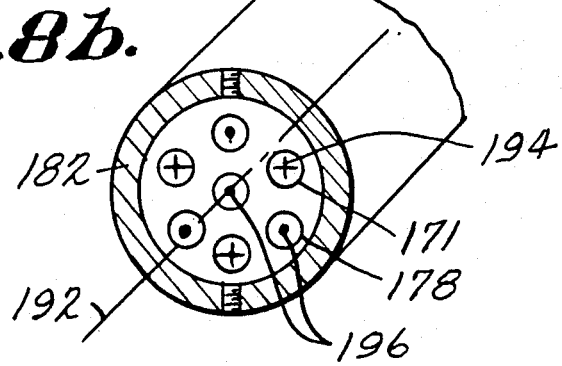
FIG. 8B is an end view taken along lines 8B—8B schematically illustrating the fiber arrangement for the single ended probe shown in FIG. 8A.
Figure 8C:
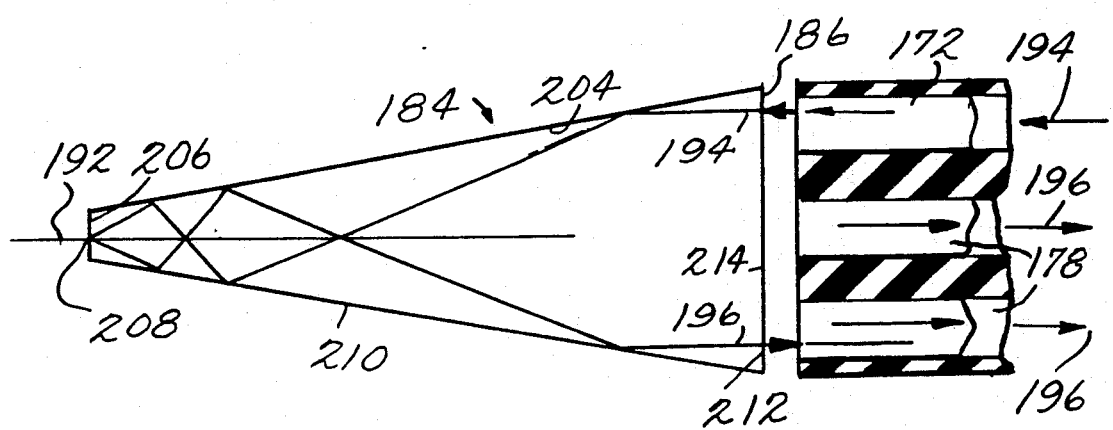
FIG. 8C is a side sectional view of the single ended probe shown in FIG. 8A having a truncated conical end.

FIGS. 8A and 8C illustrate another embodiment of the invention in which a probe 170 is formed of a pair of respective input and output fiber bundles 172 and 174. The fibers 176 in the input bundle and the fibers 178 in the output bundle 174 are joined together at a juncture or combined bundle 180. The fibers are intermingled randomly. The juncture is secured to a ferrule 182. A single ended MIR crystal 184 is also secured in a ferrule 182. The I/O end 186 of the crystal and the I/O end 188 of the two bundles of fibers are secured in proximate relationship as illustrated and may be adjusted as desired by means of a set screws 190. The I/O ends 186 and 188 may be in actual contact if desired.

FIG. 8B illustrates a simplified cross section along line 8B—8B of FIG. 8A in which the input fibers 176 and the output fibers 178 are arranged about the central axis 192 as illustrated. Input light 194 is represented by the crosses and output light 196 is represented by the dots within the respective fibers 176 and 178. For simplicity the input and output fibers are illustrated as being in alternate positions. It should be understood, however, that when the fiber bundles are intermingled, the fibers may be randomly mixed. Preferably, however, the input fibers are located near the periphery of the crystal and one of the output fibers 178 is centrally located to improve collection efficiency of output light 196. To save valuable fiber the central fiber may be omitted without serious degradation of performance. A spacer, not shown, may be substituted for the central fiber.

FIG. 8C illustrates in enlarged detail a preferred arrangement for the truncated conical single ended MIR crystal 184 shown in FIG. 8A. In the arrangement, the crystal 184 has cylindrical symmetry about the long axis 192 and is formed with tapered conical walls 204. A reflector end 206 which lies perpendicular to the long axis 192 truncates the conical walls 204. I/O end 186 is proximately coupled with respect to the fiber bundle 180 including respective input and output fibers 172 and 176. The input light 194 enters the crystal 184 at the I/O end 186 as illustrated and reflects off the walls 204 lengthwise thereof. Portions of the input light 194 are absorbed as hereinbefore described. The input light 194 is reflected by the reflector end 206 and returned to the output fibers 178 as attenuated output light 196. The reflector end 206 has a thin film of highly reflective material 208 disposed thereon. Preferably the film 208 is evaporated gold. Thus, the reflector end 206 forms a mirror for returning the input radiation. A coating 210 may be provided on the outer surface of wall 204 as hereinbefore noted in order to improve the absorption characteristic of the probe or to interact with the medium for improved performance.

The shape of the ATR element 184 and the layout of the fibers 172, 174 are important to the success of the probe. Geometries which rely on a fixed reflection angle (e.g. conical probes) may not be as effective as this configuration and may in certain circumstances reorder relative peak heights. Accordingly, the truncated cone geometry with mirrored surface 208 is preferred. The design has several significant features. The light beam 194 bounces several times from the surface 204 of the crystal, each time at a different angle (but always above the critical angle), before returning to the I/O face 186. With an appropriate choice of dimensions most of the input light 194 will return to the outer perimeter 212. The center 214 of the I/O face 186 preferably has a return or output fiber 178 to collect any stray reflected light thereby improving collection efficiency. This configuration provides maximum results and utilizes the expensive fiber most economically. As an example, the crystal 184 is a zinc selenide body being 20 mm long, with a 3 mm diameter at the I/O face 186 and 1.0 mm in diameter at the mirror face 206 with six 960 μm fibers arranged around a central fiber. The probe 170 can be made very compact. In the probe used in this example the active area of the tip is 15 mm long. The whole assembly is small and fits through the 5 mm diameter hole of a standard thermometer adaptor that is used in laboratory chemical glassware.

Another embodiment has a 5 mm barrel portion 216 (FIG. 8A), a 5 mm cone 204, 3 mm I/O face 186, and 0.5 mm reflector face 206. In this arrangement, if the input is introduced from three of the fibers, then the signal returning to the three other outer fibers and the central fiber may be calculated. Using a 20000 ray monte carlo simulation 87% (or 29% per fiber) of the returned light is received by the outer fibers versus 13% for the central fiber. These results are typical for what can be obtained with this geometry. In an exemplary embodiment a bundle of thirty (30) fibers was arranged around a dummy core of an additional seven (7) fibers in hexagonal packed array. Eleven (11) of the fibers were input fibers and nineteen (19) of the fibers were output fibers. The fibers had a 300 μm glass core surrounded by an organic cladding.

The fibers 176, 178 may be manufactured from a variety of materials including preferred chalcogenide glass having a numerical aperture in a range of about 0.2-0.8 and an exemplary numerical aperture (NA) of 0.3. The fiber has a glass core with an index of refraction (N) of about 2.8 and a plastic cladding having an index of refraction of about 1.5. An all glass fiber may be use if desired. The tapered ends of the various ATR devices herein described may have a surface lying at an angle of between 15° and 70° measured from the vertical but limited by the critical angle. A more useful range is between 25°-55° and an exemplary range is between 35°-45°. The single ended ATR devices lie in a plane perpendicular to the long axis. The large NA of the fiber helps to refract the light with respect to the long axis so that reflections occur.

The foregoing concepts have been converted into practice with a high degree of success and the following examples demonstrate in particularity their wide applicability.

EXAMPLE 1

High Pressure Autoclave Chemical Reaction

The course of the reaction of a major commodity chemical processes which operates at high pressures can be followed using the apparatus illustrated in FIG. 4 with appropriate pressure P and temperature T monitoring and stirring S apparatus. The apparatus is referred to as an optical fiber coupled cylindrical internal reflectance (OFCIR) reactor. In the reaction, cobalt catalyzed hydroformylation of olefins using a homogeneous cobalt carbonyl catalyst to produce oxo aldehydes was monitored in real time. In this reaction, 2.52 grams (0.0299 moles) of 1-hexene, 0.150 g. ($4.38 \times 10^{-4}$ moles) of dicobaltoctacarbonyl, and 6.3 mL of decane as solvent were added to the OFCIR reactor.

Figure 9:
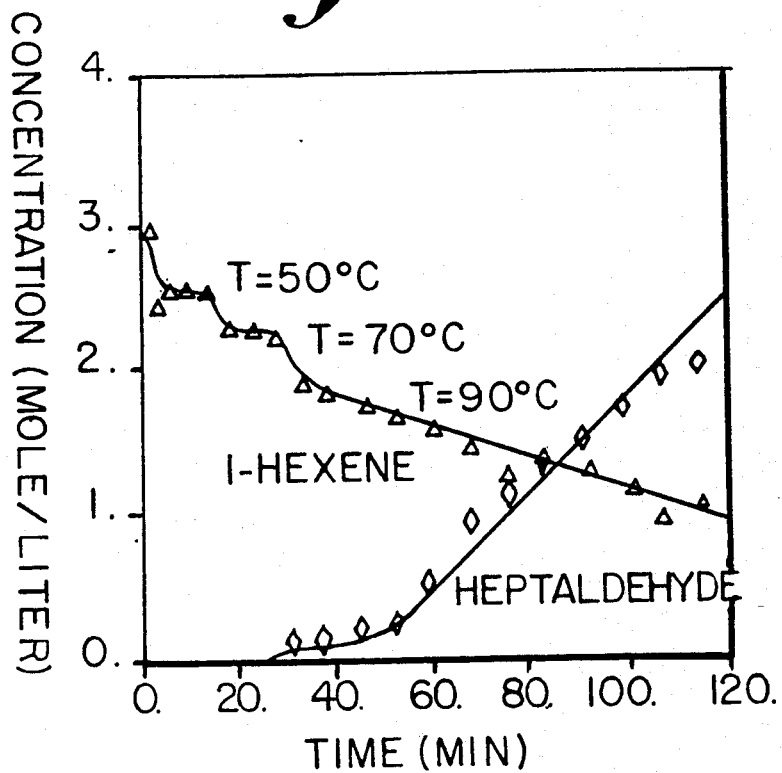
Figure 10:
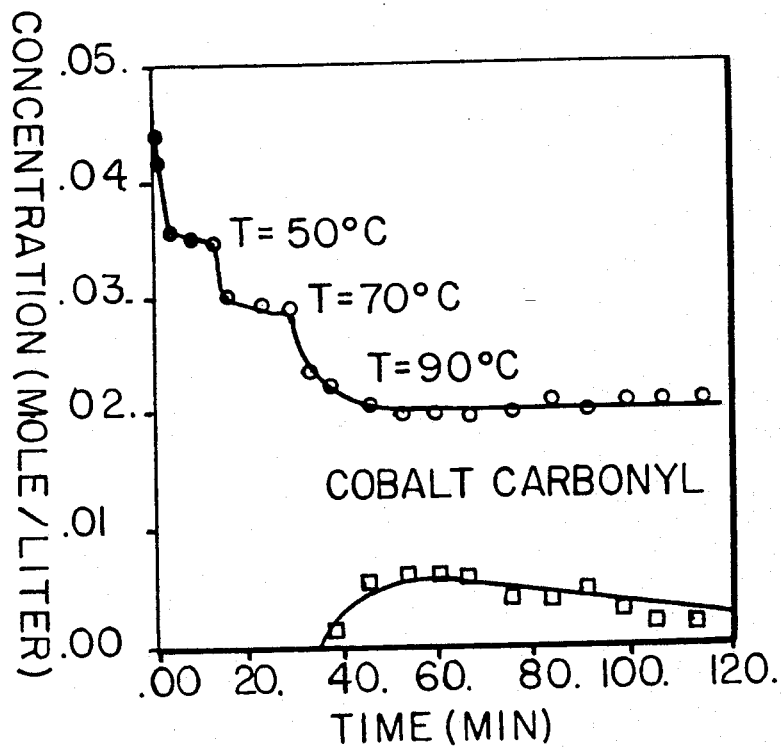

The hydroformylation process which is the subject of this example was studied by first closing the reactor after the liquid reactants were introduced in the above stated amounts, followed by pressurization of the contents with the gaseous reacting components, carbon monoxide and hydrogen to a total pressure of 1,000 psi. (6.9 MPa) using a $H_2/CO$ ratio of 1:1. The reaction was first studied as a function of temperature by examining the contents of the reactor first at 50° C. followed by intervals of monitoring at 70° C. and 90° C. By monitoring the concentration of the olefinic reactant, 1-hexene, as shown in FIG. 9, it was ascertained that the rate of reaction of olefin was slow until the 70° C. plateau had been reached. The fastest reaction rate was observed at 90° C., and simultaneous monitoring of the concentration of the desired commercial product, n-heptaldehyde, showed that a slow and constant rate of production of this product occurred between 40 minutes and 120 minutes whereupon the reaction was terminated. The capabilities of the OFCIR Reactors to monitor the composition of the active inorganic catalyst is demonstrated by the time vs concentration profile shown for the reaction in FIG. 10. This figure demonstrates that the active catalyst components were dicobaltoctacarbonyl and $C_6H_{13}COCo(CO)_4$ as identified by their characteristic IR absorption bands.

This example serves to illustrate the unusual capabilities of the OFCIR Reactors to monitor the progress of a high pressure chemical reaction in real time where the instantaneous compositions of all of the reactor contents, reactants, products, intermediates, and active catalyst components, may be quantitatively determined as a function of time and alteration in process parameters. A typical mid range infrared spectrum obtained during the course of this experiment is shown in FIG. 11. It illustrates the high quality of detection of all of the components.

EXAMPLE 2

General Laboratory Glassware Organic Chemical Reaction

This example was carried out using glassware commonly used in fine chemical, pharmaceutical, and general organic chemistry experiments with a modification to accept an optical fiber coupled cylindrical internal reflectance crystal. The reaction studied is typical of the large variety of its kind used routinely in both industrial and academic chemical laboratories.

In this series of experiments, 3.40 g. (0.0298 moles) of n-heptaldehyde and 4.0 mL of ethanol were loaded into a glass OFCIR Reactor 220 shown in FIG. 12. The reactor was equipped with a magnetic stirrer 222 and the reaction was carried out under an atmosphere of nitrogen. Then 0.70 g. ($3.01 \times 10^{-3}$ moles) of solid sodium borohydride was added, and the composition of the components of the reaction were monitored as a function of time while the contents were stirred at ambient conditions of temperature and atmospheric pressure.

One form of the glass reactor 220 represents a generic type of glass vessel through which optical fiber cables 224 and 226 are coupled to cylindrical internal reflectance rod 228 which may be embedded in the vessel by means of an apertured stopper, manufactured from a material such as polytetraflourethylene sold commercially under the trademark TEFLON (not shown). The reactor 220 was equipped with a reflux condenser, and a thermometer (not shown) through the corresponding ground glass ports 230 and 232 at the top of the reactor 220. In addition, a direct drive stirrer (not shown) may be mounted through the top ground glass joint 234. The example used magnetic stirrer 222. Heating may be applied by way of a heating tape wound around the bottom of the glass vessel or by a heating mantle made to fit the reactor (not shown). Low temperature experiments may be conducted in this equipment by placing the vessel in cooling bath.

Figure 14:
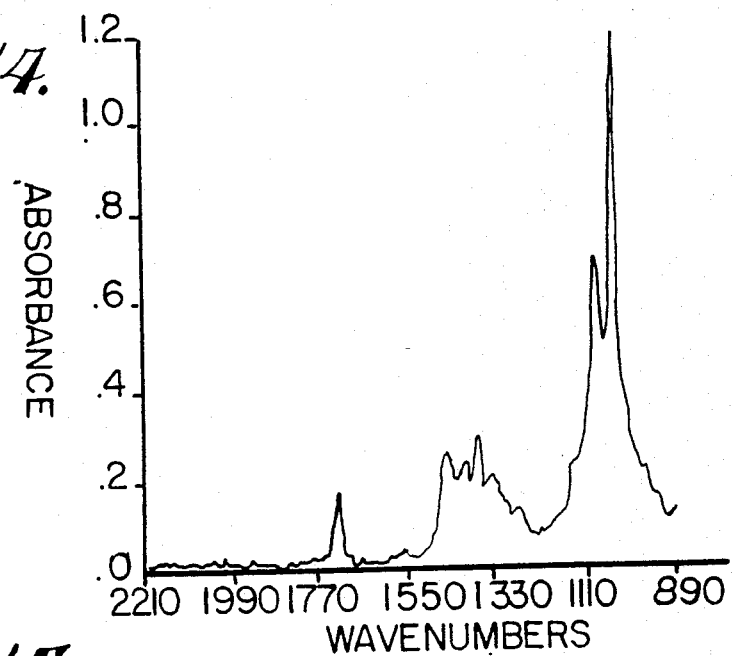

The aldehyde reduction of n-heptaldehyde to n-heptanol by sodium borohydride was followed using the above described glass reactor 220. Using this equipment the concentration of the aldehyde could be followed instantaneously as a function of the reaction time. The collection of these instantaneous data afforded the kinetic plot for the disappearance of heptaldehyde shown in FIG. 13. FIG. 14 demonstrates the quality of the in situ IR spectra at the level of 50% conversion of the aldehyde. The demonstrated spectrum is typical of those obtained throughout the entire course of the reaction.

EXAMPLE 3

Laboratory Monitoring of Inorganic, Co-ordination Chemistry and Biochemical Reactions The high pressure stainless steel reactor shown in FIG. 4 or the glass OFCIR Reactor shown in FIG. 12, may be used to monitor the course of an inorganic, co-ordination chemistry, or biochemical reaction analogous to the type performed routinely in industrial and academic research laboratories.

The high pressure OFCIR reactor 64 shown in FIG. 4 was used to perform an inorganic reaction for the conversion of dicobaltoctacarbonyl to [Co(CH₃OH)₆]-[Co(CO)₄]₂ at atmospheric pressure and room temperature. As a feedstock to this reaction, 1.03 g. (3.01×10⁻³ moles) of dicobaltoctacarbonyl was dissolved in decane in a dry box. Six mL of this solution were loaded into the autoclave, and it was then sealed. An excess of methanol, 3.0 mL, was then added to the stirred reaction mixture. Immediately, the contents of the reactor were monitored by the OFCIR method as a function of reaction time.

Figure 15:
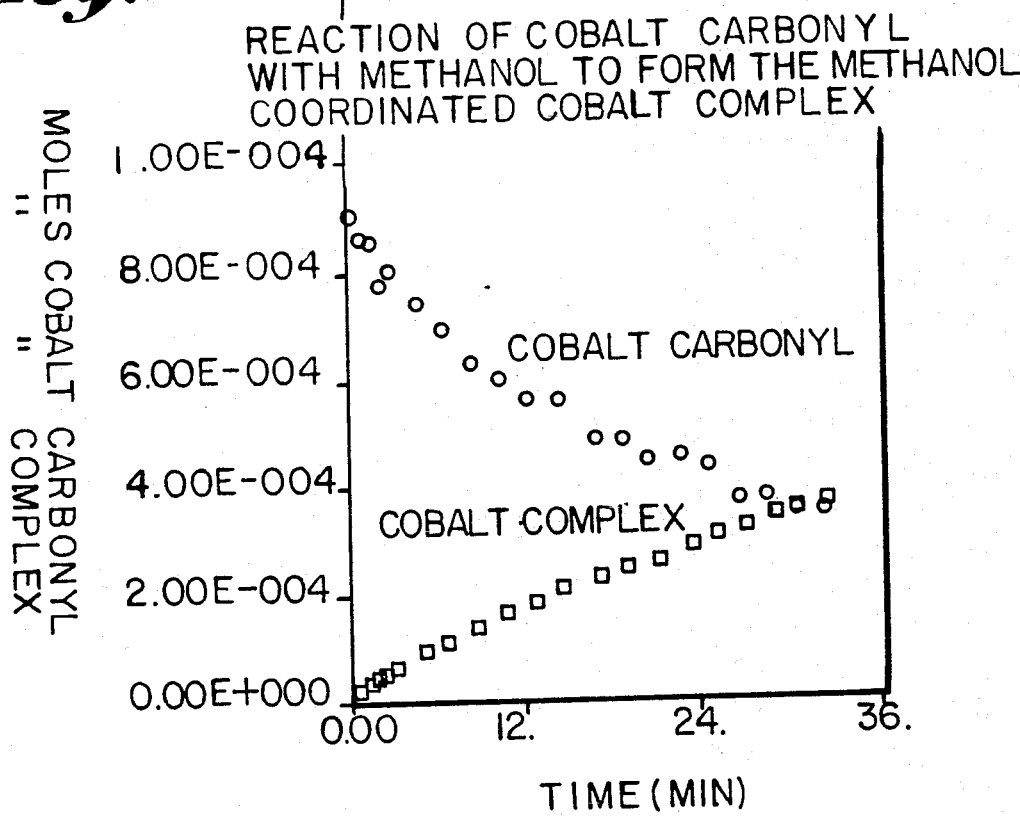
Figure 16:
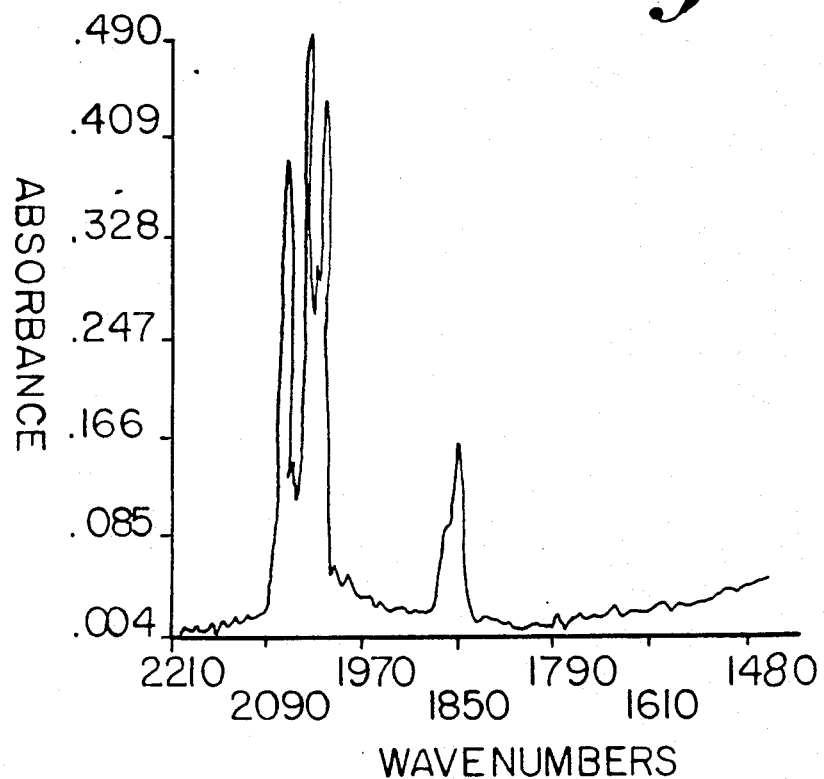
Figure 17:
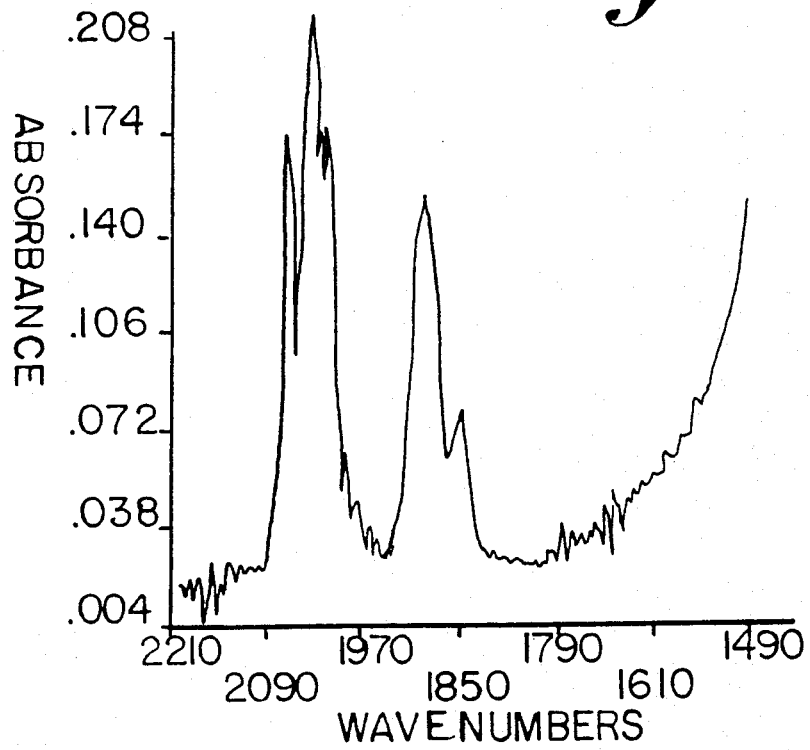

FIG. 15 illustrates the quality of the kinetic data obtained from monitoring both the reactants and formed products of this reaction. The disappearance of dicobaltoctacarbonyl was readily followed as was the appearance of the product, $[Co(CH_3OH)_6][Co(CO)_4]_2$ by an electronic integration of bands characteristics of the individual components. The in situ IR spectrum of the stirred mixture at the start of the reaction is demonstrated in FIG. 16, and the spectrum at 30% conversion of the dicobaltoctacarbonyl is illustrated in FIG. 17.

EXAMPLE 4

Single Ended Immersion Geometry

A single ended probe configuration offers considerable advantages in adaptability and ease of use over the straight-through CIR geometry use in the previous examples. A single ended immersion probe 200 (FIG. 8C) was constructed and tested.

Figure 18:
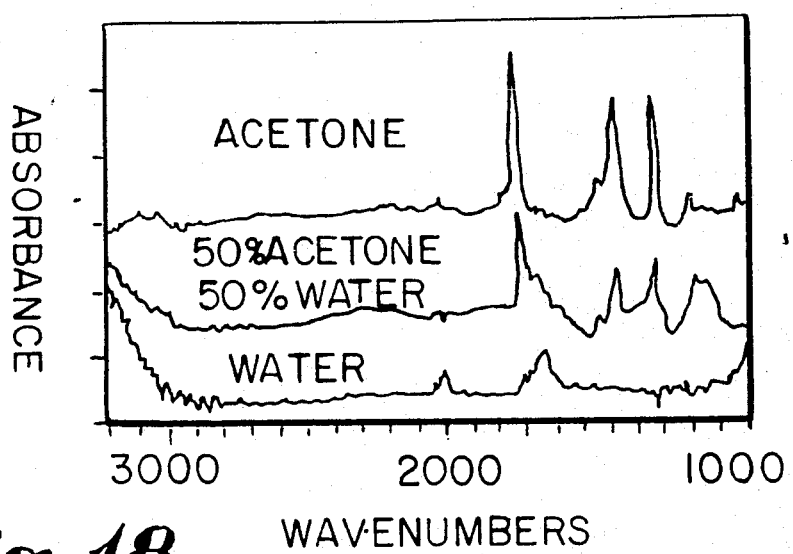
Figure 19:
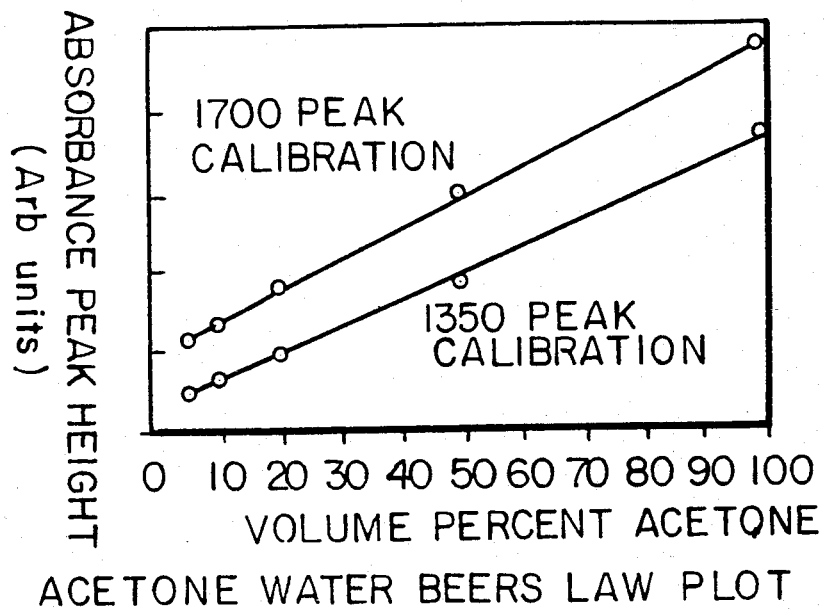
FIG. 19 is a Beers law plot for acetone and water mixtures determined using the single ended probe.

To evaluate the effectiveness of the probe for qualitative and quantitative chemical analysis a series of samples were prepared by mixing known volumes of water and acetone together (10 ml of water and 10 ml of acetone mixed give a 50% solution). A typical spectrum of such a mixture is given in FIG. 18. This spectrum was collected in 3.6 minutes on a typical commercial FTIR (Mattson Galaxy series). A Beers law plot (FIG. 19) of the uncorrected and unsmoothed absorbance of the 1350 and 1700 wave number peaks shows that a good very linear calibration can be obtained.

Figure 20:
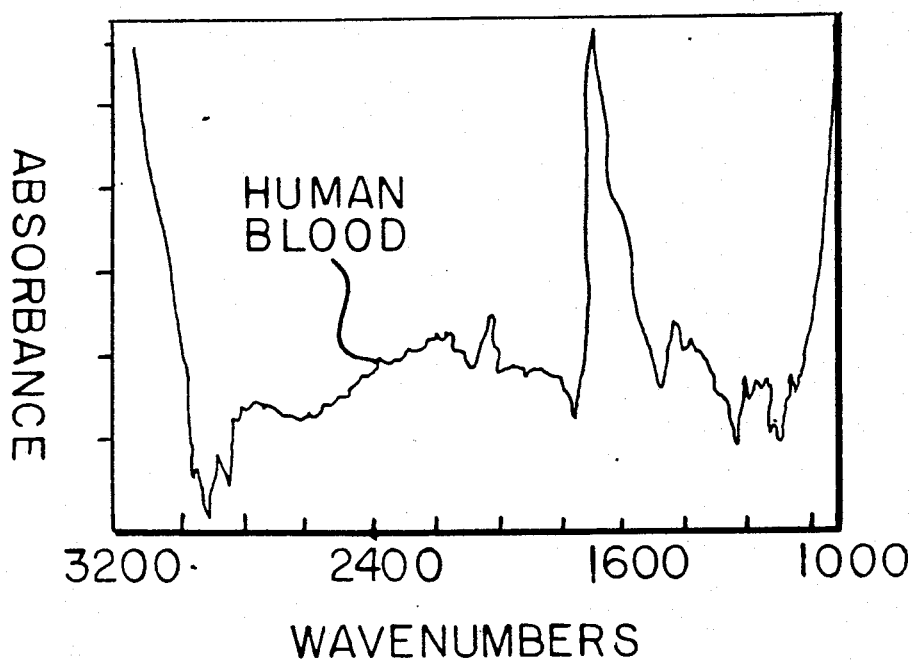
Figure 21:
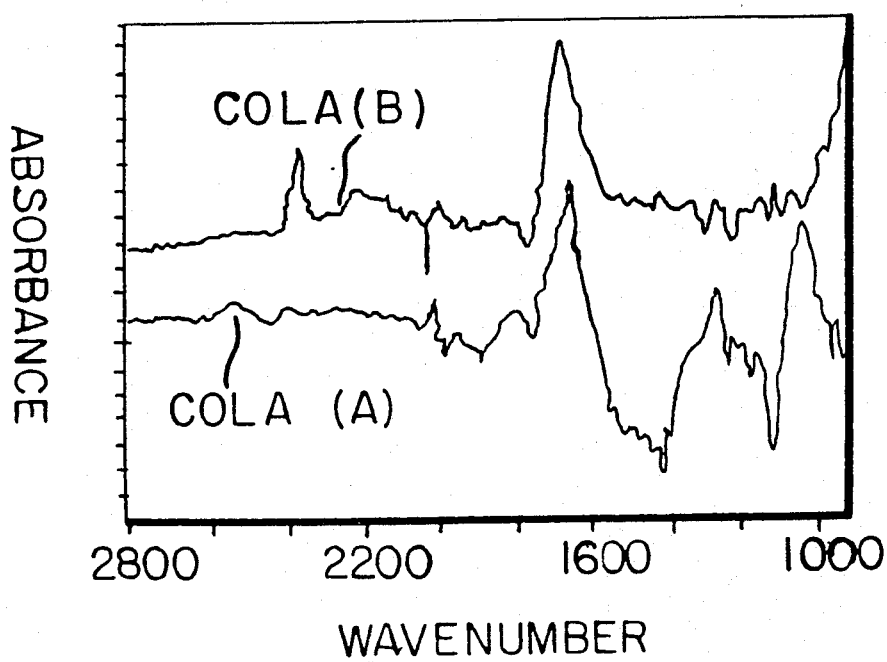

Two additional spectra are shown for illustrative purposes, a spectrum of whole human blood (FIG. 20) and a commercial cola compared to its diet companion (FIG. 21).

It should be apparent that the present invention is not limited to the specific examples herein above. The invention has general applicability to remote fiber optic coupled spectrometer probe assemblies which has many advantages over the prior art. For example, the sample may be located remote from the spectrometer instrument without moving the instrument physically to the location of the sample or vice versa. The remote location of the sample avoids risking contamination or damage to the more expensive instrument at the sacrifice of the much lower cost expendable remote fiber optic probe. The remote fiber optic probe design provides for efficient coupling of the probe illumination from the spectrometer to the sample with a minimum of optical elements and surfaces between the spectrometer optical source and the sample. The fiber optic-MIR cell design provides for a minimum distortion internal reflection spectra with excellent linearity and efficiency as a function of sample index. The remote fiber optic probe can be imbedded in a process system for true on-line in situ process monitoring or used to determine the contents of containers such as toxic waste drums.

While there has been described what at present is considered to be the preferred embodiment of the present invention it will be apparent to those skilled in the art that various changes and modifications may be made therein without the departing from the invention and it is intended in the appended claims to cover all such changes and modifications as forward in the true spirit and scope of the invention.

What is claimed is:

1. A probe operative in th infrared region of the EM spectrum for in situ real time sensing of the absorption of IR energy in a sample comprising:
an attenuated total reflection (ATR) crystal element having an input end portion for receiving IR energy and an output end portion for transmitting attenuated IR energy, said ATR element having wall portions disposed along a central or long axis thereof, said IR energy being reflected along the element in a direction transverse to the central axis;
a plurality of infrared transmitting fibers in the form of a cylindrical bundle at the input end portion and the output end portion of the ATR element, said bundle of fibers having end faces disposed in direct contacting abutment with the ATR element for transmitting and receiving IR energy into and out of the element, said bundle arranged in a cluster of individual fibers, said bundle centered on an axis common with the central axis of the ATR element, said fibers having a relatively high numerical apertures for spreading transmitted energy so that a portion of said energy enters the ATR element at an angle less than the critical angel for facilitating total internal refection by the wall portions of the element and for receiving a sensible amount of IR energy from said ATR element.

2. The probe of claim 1 wherein the input end portion and the output end portion of the ATR element are at opposite ends of the crystal.

3. The probe of claim 1 wherein the input end portion and the output end portion of the ATR element are at the same end of the crystal.

4. The probe of claim 3 further comprising a reflector end for the crystal disposed at an angle to the long axis and located at an end of the crystal remote for the input end and output end portions for returning energy from the input to the output.

5. The probe of claim 4 wherein the reflector end is a conical taper.

6. The probe of claim 4 wherein the reflector end is a frustroconical taper having a planar end perpendicular to the long axis and a mirror surface disposed on said planar end for reflecting energy therefrom.

7. The probe of claim 1 wherein at least one of the input end portion and output end portion is located in a plane transverse to the central axis.

8. The probe of claim 1 further comprising coupling means for connecting the ATR element and the bundle of fibers.

9. The probe of claim 1 wherein the ATR element and the fibers have respective indices of refraction which differ from each other by less than about 0.5.

10. The probe of claim 1 wherein the ATR element and the fibers have respective indices of refraction which differ from each other by about 18%.

11. The probe of claim 1 wherein the fibers comprise a selected number of input fibers for carrying IR energy to the ATR element and a selected number of output fibers for carrying the IR energy from the ATR element, said fibers being randomly intermingled.

12. The probe claim 1 wherein the fibers comprise a selected number of input fibers for carrying IR energy to the ATR element and a selected number of output fibers for carrying the IR energy from ATR element, said fibers being alternately intermingled.

13. The probe of claim 1 wherein the fibers comprise a selected number of input and output fibers, said fibers are arranged at one end of the ATR in an annular ring about a spacer element.

14. The probe of claim 13 wherein the spacer element is an output fiber.

15. The probe of claim 13 wherein the fibers are alternately intermingled.

16. The probe of claim 13 wherein the fibers are randomly intermingled.

17. The probe of claim 1 wherein the fibers are butt coupled to the input and output end portions of the ATR element in the plane of said end faces.

18. The probe of claim 1 wherein the fibers are coupled to the ATR element in a plane perpendicular to the long axis.

19. The probe of claim 1 wherein the fibers have a numerical aperture resulting in a relatively wide cone of acceptance thereby spreading IR energy at the input end portion of the ATR element, and resulting in a wide angle of acceptance for IR energy at the output end portion of the ATR element.

20. The probe of claim 1 wherein the ATR element and the bundle of fibers does not exceed a diameter of about 5 mm corresponding to the diameter of a standard laboratory thermometer.

21. The probe of claim 1, wherein each fiber has a numerical aperture ranging from about 0.2 to about 0.8.

22. The probe of claim 1, wherein each fiber has a core diameter of about 300 $\mu$m.

23. The probe of claim 1, wherein the ATR has a tapered input and output end having an angle ranging from about 15 to about 70 degrees.

24. The probe of claim 23, wherein the angle ranges from about 25 to about 55 degrees.

25. The probe of claim 24, wherein the angle ranges from about 35 to about 45 degrees.

26. A probe comprising:
an optical fiber cable for carrying a light wave coupled to one end of a doubled ended cylindrical internal reflectance crystal through which light is directed into the crystal and an optical fiber cable coupled to the other end of the crystal wherein the optical fiber cable comprises multiple fibers connected at one end to the cylindrical internal reflectance crystal for establishing an angle of incidence of the light wave with the crystal while ensuring a high percentage of the light being reflected and redirected into the other end of the fiber cable, a portion of the fibers is connected to a light source and the remaining portion of the fibers is connected to a detector appropriate for analyzing the wavelength of light of interest.

27. An optical probe operative for in situ real time sensing of th absorption optical energy in a sample within a vessel comprising:
an attenuated total reflection (ATR) crystal element having an input end portion for receiving the energy and an output end portion of transmitting attenuated energy, said ATR element having wall portions disposed along a central or long axis thereof, said energy being reflected along the element in a direction transverse to the central axis;
a bundle of optical fibers at the input end and the output end of the ATR element, said bundle arranged in a cluster of individual fibers, said bundle centered on an axis common with the central axis of the ATR element, and said bundle of fibers having end faces disposed proximate the ATR element for transmitting and receiving the energy into and out of the element, said fibers having a relatively high numerical aperture for spreading transmitted energy so that a portion of said energy enters the ATR element at an angle less than the critical angle for facilitating total internal reflection by the wall portions of the ATR element and for receiving a sensible amount of energy from said ATR element.

28. The probe of claim 27 wherein the crystal is located in an opening in the vessel further comprising a gland having an aperture for snugly receiving the crystal therein, said gland sealably locatable in the opening.

29. The probe of claim 27 wherein the vessel is pressurized and the opening is a bore having a threaded portion and a stepped portion, and the gland is threadably located in the threaded portion further comprising an apertured annular insert locatable coaxially between the threshold portion and the stepped portion for compressible abutment therebetween, for enabling a hermetic seal.

30. The probe of claim 29 wherein the opening has a taper portion and the insert is taped to conform therewith.

31. The probe of claim 29 wherein the insert is an O-ring.

32. The probe of claim 29 wherein the gland is a rubber stopper.

33. A probe comprising:
an optical fiber cable for carrying a light wave, coupled to one end of a doubled ended cylindrical internal reflectance crystal through which light is directed into the crystal and an optical fiber cable coupled to the other end of th crystal for receiving an attenuated light wave from the crystal wherein the optical fiber cable comprises multiple fibers connected at one end to the cylindrical internal reflectance crystal for establishing an angle of incidence of the light wave with the crystal while ensuring a high percentage of the light being reflected and re-directed into the other end of the fiber cable, a portion of the fibers is connected to a light source and the remaining portion of the fibers is connected to a detector appropriate for analyzing the wavelength of light of interest.

* * * * *